(12) United States Patent
Petrov

(10) Patent No.: US 11,160,895 B2
(45) Date of Patent: Nov. 2, 2021

(54) AUTOMATED MODULAR ENVIRONMENT MODIFICATION DEVICE

(71) Applicant: INVENTURE LABS LLC, Jersey City, NJ (US)

(72) Inventor: Stan Petrov, Alexandria, VA (US)

(*) Notice: Subject to any disclaimer, the term of this patent is extended or adjusted under 35 U.S.C. 154(b) by 0 days.

(21) Appl. No.: 16/461,309

(22) PCT Filed: Feb. 7, 2017

(86) PCT No.: PCT/US2017/016836
§ 371 (c)(1),
(2) Date: May 15, 2019

(87) PCT Pub. No.: WO2018/093407
PCT Pub. Date: May 24, 2018

(65) Prior Publication Data
US 2020/0069833 A1    Mar. 5, 2020

Related U.S. Application Data

(60) Provisional application No. 62/424,783, filed on Nov. 21, 2016.

(51) Int. Cl.
| | | |
|---|---|---|
| A61L 9/12 | (2006.01) | |
| A61L 2/22 | (2006.01) | |
| A61L 2/24 | (2006.01) | |
| A61L 9/03 | (2006.01) | |

(52) U.S. Cl.
CPC ............ *A61L 9/122* (2013.01); *A61L 2/22* (2013.01); *A61L 2/24* (2013.01); *A61L 9/03* (2013.01); *A61L 2202/14* (2013.01); *A61L 2202/15* (2013.01); *A61L 2202/16* (2013.01); *A61L 2202/25* (2013.01); *A61L 2209/111* (2013.01);
(Continued)

(58) Field of Classification Search
None
See application file for complete search history.

(56) References Cited

U.S. PATENT DOCUMENTS

| 9,089,620 B2 | 7/2015 | Henriot |
|---|---|---|
| 2004/0231636 A1 | 11/2004 | Ricordi |

(Continued)

FOREIGN PATENT DOCUMENTS

| CN | 204958485 | 1/2016 |
|---|---|---|

OTHER PUBLICATIONS

PCT International Search Report and Written Opinion of the Searching Authority, dated Apr. 21, 2019, 8 pages.

*Primary Examiner* — Jelitza M Perez

(57) ABSTRACT

A modular environment modification device receives different cores for performing different functions such as dispensing decontaminant agents. These cores are contained within a housing that can communicate with other like devices and with remote devices such as iOS or Android powered smart devices. Communication between multiple like devices provides the ability to accommodate spaces of varying size. Sensors within each device monitor the environment, sense temperature and pressure, the presence of certain pathogens, and sound. Sensed information is used by the device to make decisions, like suspension of the decontamination process. Sensed information is sent to smart devices which perform various interfacing or data collection functions.

10 Claims, 18 Drawing Sheets

(52) U.S. Cl.
CPC ... *A61L 2209/133* (2013.01); *A61L 2209/134* (2013.01); *A61L 2209/212* (2013.01)

(56) References Cited

U.S. PATENT DOCUMENTS

| | | | |
|---|---|---|---|
| 2005/0279854 A1* | 12/2005 | Martens, III | B05B 17/0684 239/44 |
| 2006/0260609 A1* | 11/2006 | Bruening | A61M 16/1075 128/200.24 |
| 2012/0093691 A1 | 4/2012 | Mole | |
| 2014/0056765 A1* | 2/2014 | Henriot | A61L 9/03 422/120 |
| 2017/0119919 A1* | 5/2017 | Hsiao | A61M 21/00 |

* cited by examiner

AUTOMATED MODULAR ENVIRONMENT MODIFICATION DEVICE

CROSS REFERENCE TO RELATED APPLICATIONS

This application claims the benefit of provisional patent application No. 62/424,783 filed Nov. 21, 2016 for Multi-Functional modules Core (MMC) Platform, the entirety of which is incorporated herein by reference.

BACKGROUND OF THE INVENTION

1. Field of the Invention

The present invention relates to improvements in environment modification devices and more particularly pertains to new modular environment modification devices wherein functionality of the device can be modified by changing the modules.

2. Description of Related Art

Known environment modification devices, like decontamination devices for example, are largely expensive to purchase and operate. The design philosophy of these known devices lead to devices lacking flexibility in terms of size and function, devices difficult to move, devices that use unnecessarily complex systems, that increase the likelihood of component failure, increasing service and repair cost. Known devices require routine implementation of proprietary software that prevents the ability to interface with other third party devices. These restrictions limit data handling and accountability, making these devices highly specialized and expensive.

Known decontamination equipment is generally sluggish, expensive to buy and unable to rapidly respond to changes in the environment. A user of such known devices works in dangerous, frustrating environments of ever increasing complexity. These known devices fail to deal with the threat of emerging pathogens.

SUMMARY OF THE INVENTION

The present invention allows a user to combine or interchange functional modules, which comprise specialized hardware grouped by function and individually packaged housing. These functional modules are inserted into a module receiver unit that contains connections and support hardware, allowing the functional modules to interconnect with a main micro controller, housed in the module receiver. The modular device is made up of multiple modules, each performing a different function. The device includes sensors and transmitters for communication between other devices, as well as sensing its environment. The device includes a trigger system that can be externally activated or activated by environmental factors sensed by the sensors on the device, based on user-defined parameters.

The automated modular device uses support and functional hardware that allows it to perform multi-step processes, provide platform versatility and system upgradability. The configuration of the device allows it to parallel the function of existing devices and integrate the device's hardware and software with like devices, providing for scalability and convenience in a platform for decontaminating certain environments.

The modular device is utilized for decontamination by having multiple functional cores with different functions such as dispensing decontaminant agents to neutralize harmful pathogens that may be present on various surfaces or in the air, or neutralizing harmful chemicals that may be present in the air, for example. These functional modules are contained within a housing which can communicate with other like devices such as iOS or Android powered smart devices, for example. Communication between multiple devices allows for use of multiple devices, for example, at one time for decontamination of spaces of varying size. Sensors within each device are capable of monitoring the environment to sense temperature and pressure changes, the presence of certain pathogens, and sound, for example. This information is used by the device to make decisions, including suspension of the decontamination process, for example. Sensor information may be sent to smart devices which can perform various interfacing or data collection functions. This allows a user to control the start of a decontamination process and the functionality of the hardware and software in the modules of the device. The device can be programmed to release decontaminant agents under certain pre-defined conditions triggered by the sensors. The device can determine if a decontamination processes should be interrupted by suspending the release of a decontamination agent, or send a warning.

The modular device of the present invention is less expensive, compact, lightweight, multi-functional and capable of remote or autonomous triggering by integrated smart electronics, allowing for increased security, safety and data collection.

BRIEF DESCRIPTION OF THE DRAWINGS

Many of the attendant advantages of this invention will be readily appreciated as the same becomes better understood by reference to the following detailed description considered in conjunction with the accompanying drawings in which like reference numerals designate like parts throughout the figures thereof and wherein.

DETAILED DESCRIPTION OF THE PREFERRED EMBODIMENTS

Figure 1:
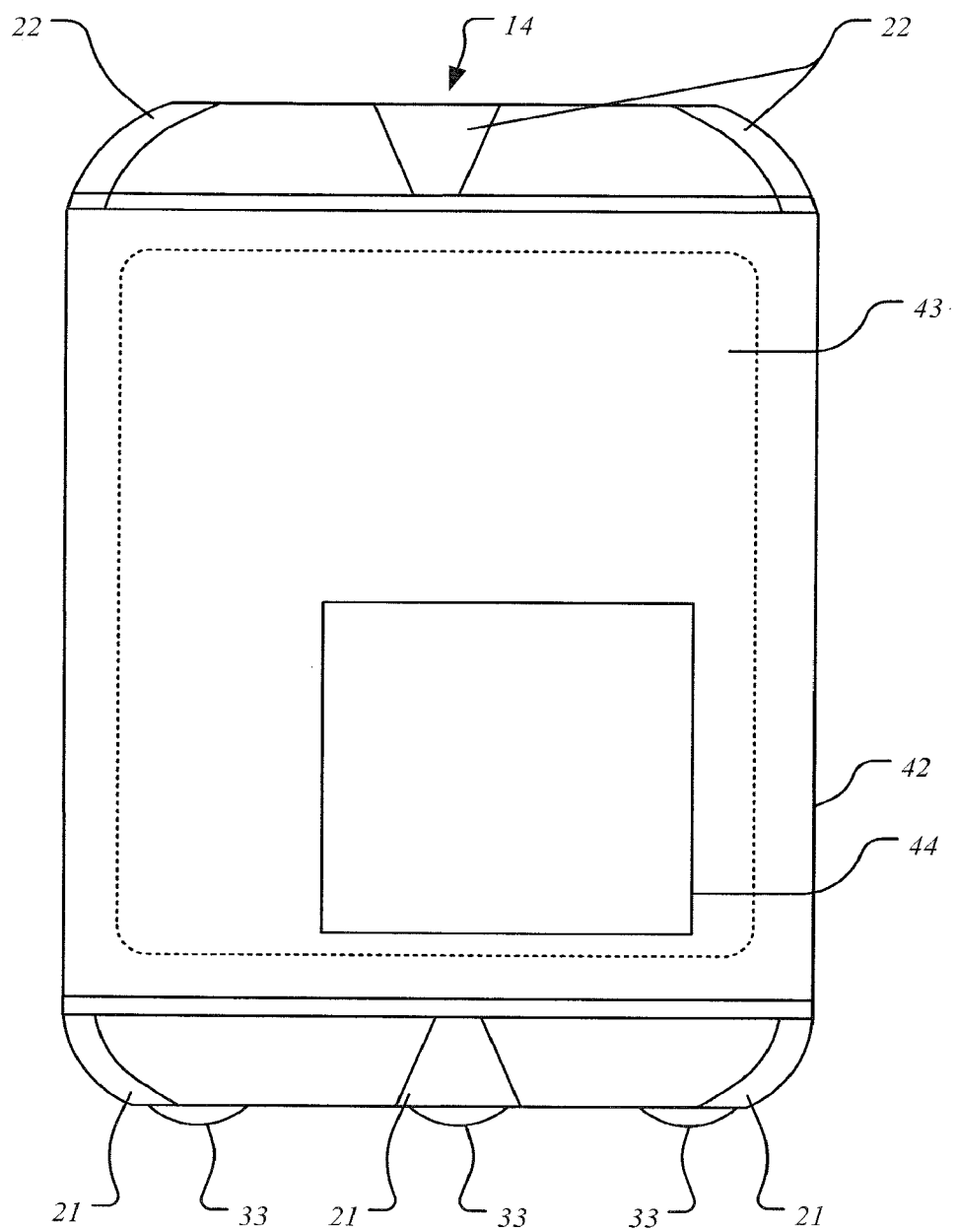
FIG. 1 is a front view of a modular device according to a preferred embodiment of the present invention.

A preferred embodiment of the automated modular device 14 is shown in FIG. 1. Some of its features include reflective light assemblies 21 strategically placed around the bottom of the device and reflective light assemblies with an optional optical thermopile 22 placed evenly around the top. These reflective light assemblies 21, 22 are strategically placed around the edges, exposing the device to a 360 degree view of the surrounding environment. The reflective light assemblies 21, 22 perform multiple functions which will be described hereafter.

Figure 2:
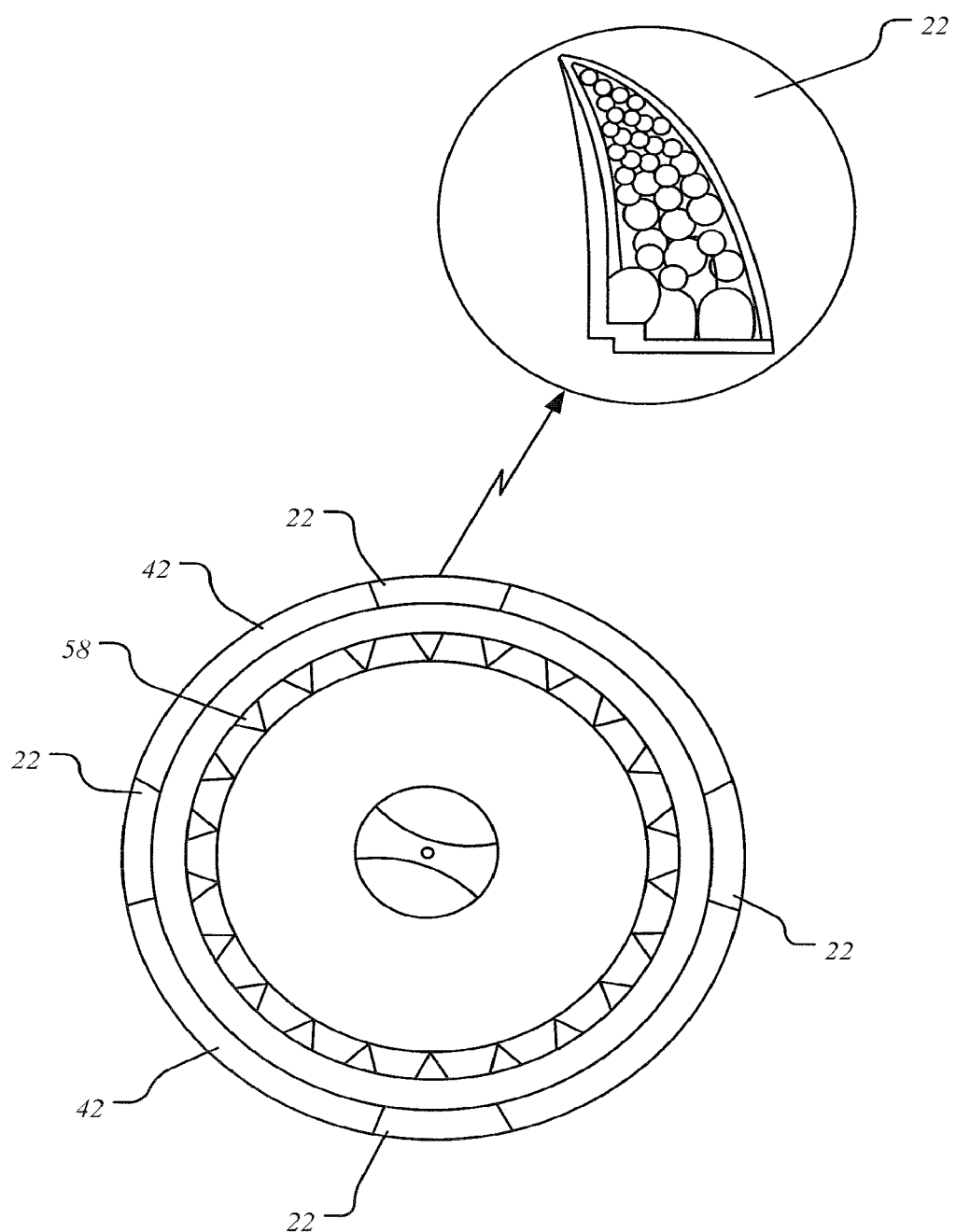
FIG. 2 is a top view of the modular device showing a light assembly.
Figure 3:
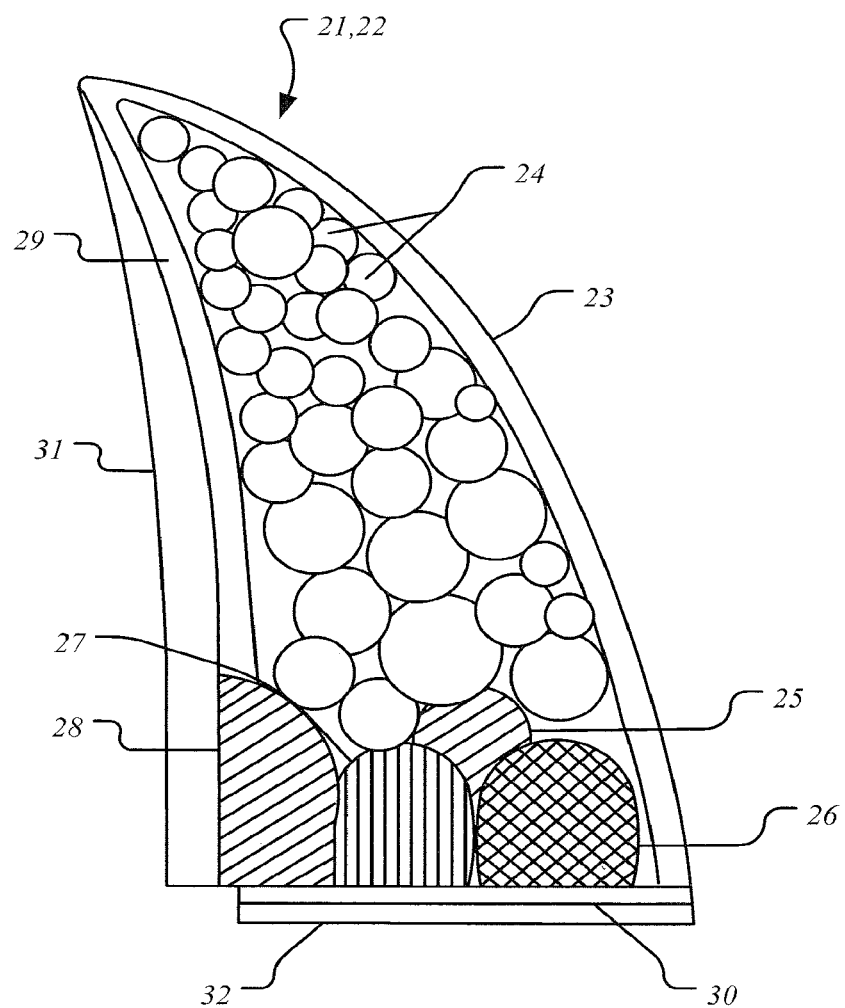
FIG. 3 is a sectional view of the light assembly of FIG. 2.

To further understand the multi-functional nature of the reflective light assembly 21, 22 (FIG. 1, FIG. 2, and FIG. 4), it is important to understand the main functional components which are shown in saggital cross section in FIG. 3. Describing from the outside in, the reflective light assembly 21, 22 consists of a light conductive layer 23. This light conductive layer 23 allows light to pass through it into the area filled with light scattering particles 24. The main function of particles 24 is to scatter light towards the various integrated sensors and disperse signals from the sensors. These integrated sensors include light sensing and emitting assembly 25, receiving diode assembly 26, transmitting emitting diode assembly 27, and motion sensor assembly 28. An upper light reflective layer 29 and a lower light reflective layer 30 are added to the back reflective light assembly housing 31 and reflective light assembly base 32 respectively. These, together with light conductive layer 23 make up the reflective light assembly housing of light assembly 21, 22. The multipurpose components of the light assembly 21, 22 use software and hardware for emitting multicolor visible light to a user, to provide visual feedback. Furthermore the reflective light assembly 21, 22 allows the device to detect changes in light intensity and motion via the motion sensor assembly 28 and light sensing and emitting assembly 25. Human presence is thus detected. This detection of a human presence is utilized to interfere with the trigger mechanism in the device for termination of a decontamination cycle. This fail safe option prevents injury to any human in the area of the device.

Another function of the reflective light assembly 21, 22 is the ability to exchange information between units, by light communication between units through the receiver diode assembly 26 and transmitting diode assembly 27. These diode assemblies preferably make use of infrared communication. Therefore one unit's transmitting diode assembly 27 can pair with another unit's receiving diode assembly 26 and vice versa. This enables communication between different devices and the use of multiple devices in a coordinated manner to perform a single task. Furthermore, this communication capability allows the device to interface with other devices capable of infrared light communication.

FIG. 1 shows a side view of support bearings 33. The placement of bearings 33 on the device 14 is shown in a bottom view of the device 14 in FIG. 4. The bearings 33 perform the function of wheels, as well as provides space between the bottom of device 14 and a support surface, a floor for example, allowing air to flow freely underneath and around the device 14.

Figure 5:
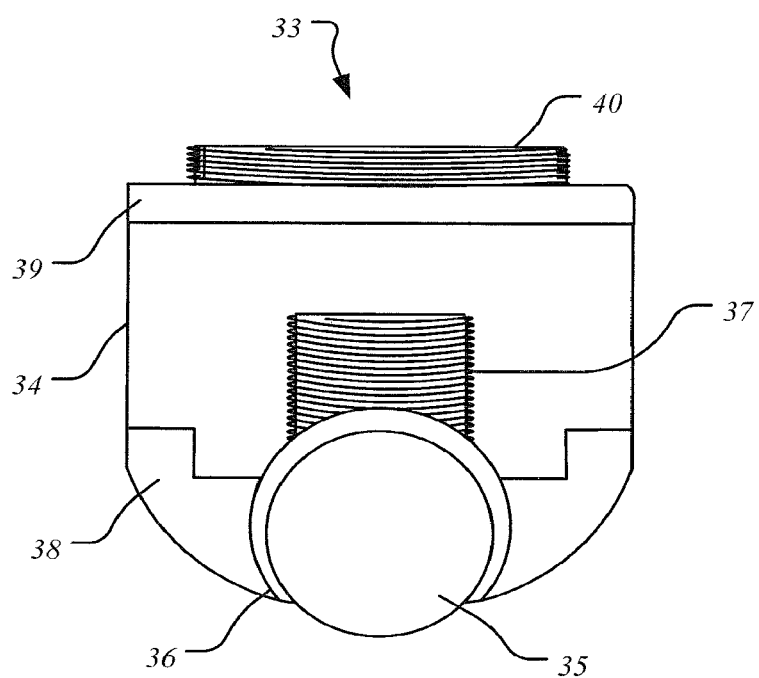
FIG. 5 is a cross sectional view of a support for the modular decontamination device.

The functional components of the bearings 33 is illustrated in cross section on FIG. 5. The bearing housing 34 is the largest component of the bearing assembly 33. The bearing housing 34 is preferably made of a strong, hard, non-elastic material such as a metal or rigid plastic, for example. The functional components of the bearing assembly 33 preferably are a ceramic ball bearing 35, a frictionless plate 36, a compression plate spring tensioner 37, a compression ball bearing lock 38, an optional frictionless o-ring plate 39 and a threaded stud 40 for attaching to the base of the housing of the device 14.

In terms of functionality, the bearing assembly 33 is similar to an animal's bone joints. The force exerted on the ceramic ball bearing 35 is distributed evenly throughout the housing 34. The frictionless plate 36 acts like a cartilage, not only distributing the force more evenly by deforming, but also allowing the ceramic ball bearing 35 to rotate omnidirectionally. In order to keep the frictionless plate 36 in place and limit the ceramic ball bearing 35 free movement when no load is applied, a compression plate spring tensioner 37 applies a small amount of force to the ball bearing 35, thus keeping the components under tension. Furthermore, an optional frictionless o-ring plate 39 prevents locking during removal and installation of the bearings 33 to the main frame 41 (FIG. 4) by threaded stud 40. The bearings 33 parallel and surpasses industry standard in terms of ergonomics, support and movement of the device 14, eliminating the need for the use of a wheel and axle assembly.

Figure 6:
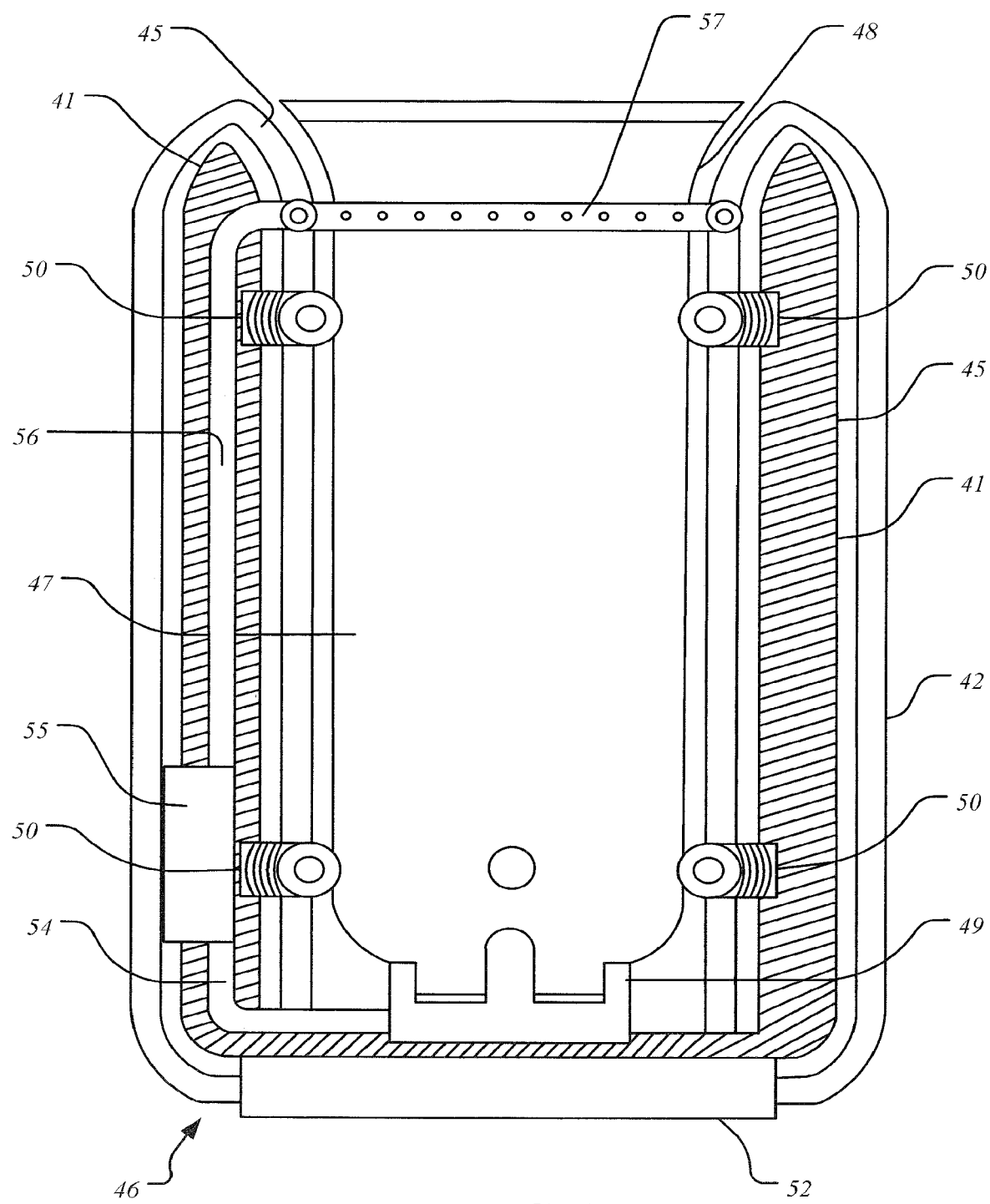
FIG. 6 is a cross section of the modular device of FIG. 1 showing the major components.

FIG. 1 shows the outer most layer of the device 14, the outer housing/shell 42. The outer housing/shell 42 is designed to enhance user interaction by including one or more areas 43 on the outer housing 42 that are semipermeable to light. This allows a user to add a visual feedback device 44, such as an LCD display, smart device or serial display device for example. The outer housing/shell 42 has capacitive touch capabilities. Thus a user can utilize, for example, functional buttons that interact with the visual feedback device 44 which is displaying data. The housing 42 is preferably shaped as a cylinder, as shown in FIG. 2 and in FIG. 4. This cylindrical shape is adapted to the rest of the major components of the device 14, as can be seen in FIG. 6, for example. FIG. 6 is a coronal cross section of the device 14, showing the major internal structure and their spatial relationships.

FIG. 6 shows the device 14 in coronal cross section. Starting from outside in, the outer structure is outer housing/shell 42. A main frame 41 and an inner shell wall 45 are located under the outer housing/sheet 42. This structure is the core receiver 46 shown in a coronal cross section in FIG. 6. The main frame 41 is illustrated in greater detail in FIG. 7. This structure provides structural support and all essential hardware components for performing the function of discharging a pressurized substance as used in the preferred embodiment for decontamination. The functional core 47 in the preferred embodiment is a pressurized decontamination substance containing container (FIG. 6) which fits into a central duct 48, shown in FIG. 9, enclosed by an inner shell wall 45 shown in cross section in FIG. 9.

Figure 7A:
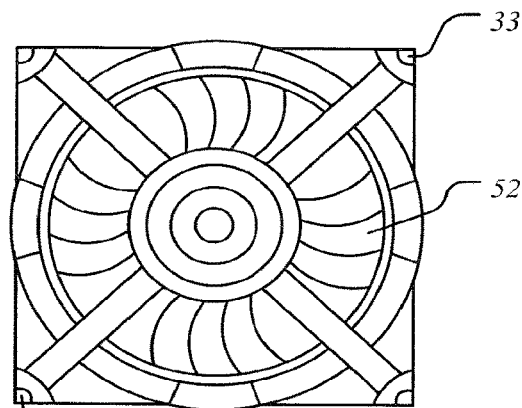
FIG. 7A is a plan view of the fan assembly.
Figure 7:
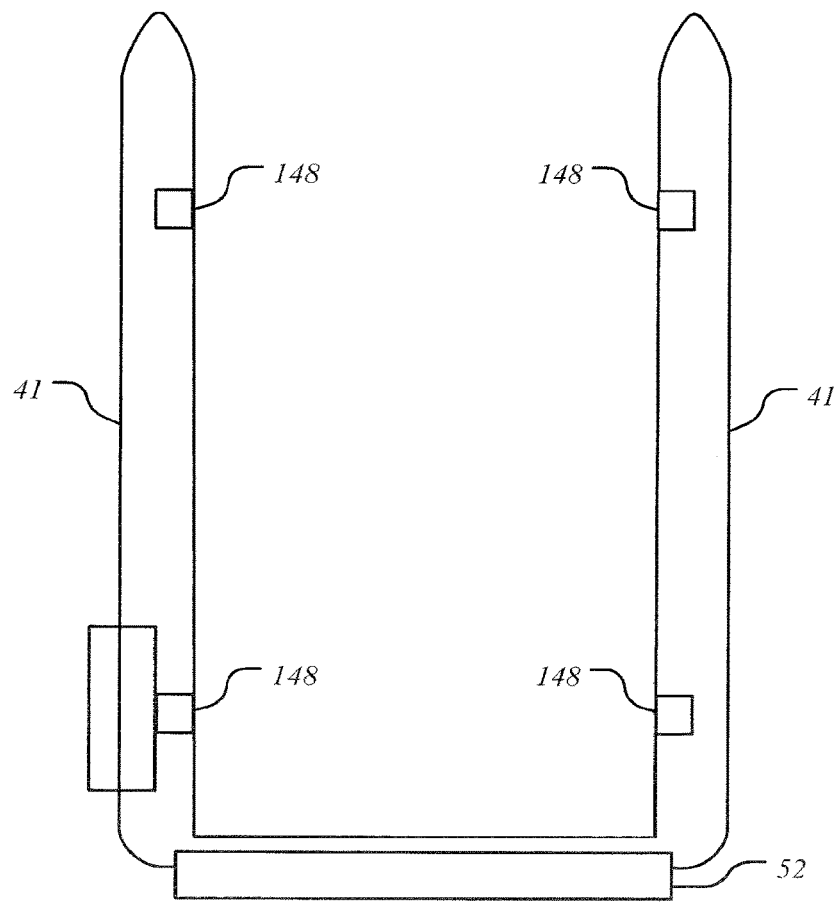
FIG. 7 is a cross section of the modular device of FIG. 1 showing the module receiver and main frame.
Figure 8A:
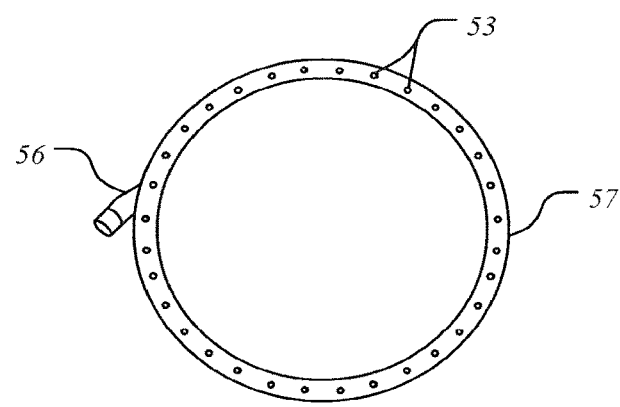
FIG. 8A is a plan view of a dispersion ring.
Figure 8:
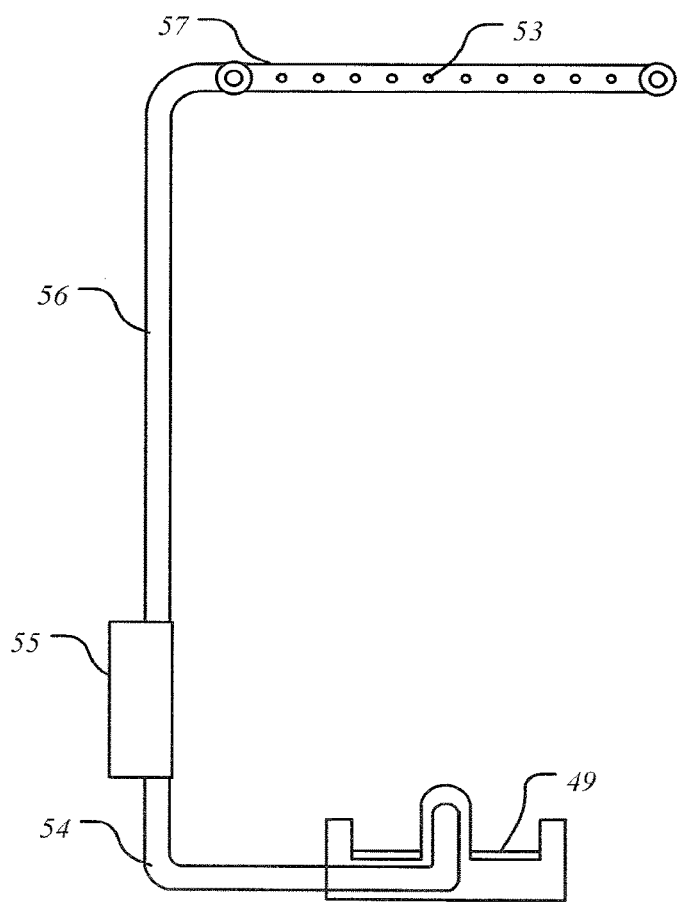
FIG. 8 is a cross section of the main components of the injection and dispersion assembly.
Figure 9:
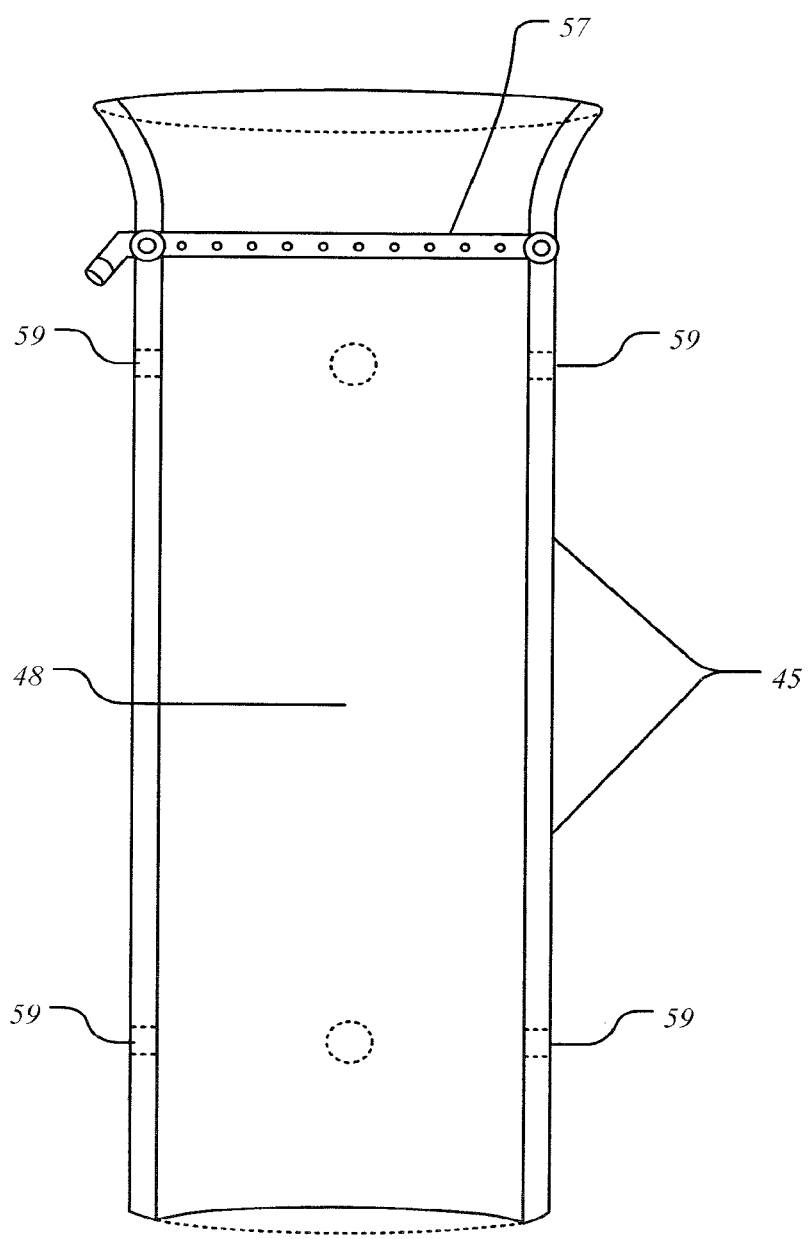
FIG. 9 is a cross section of the device of FIG. 6 showing the inner duct shell.

The base of the functional core 47 is secured by a threaded core receiver 49 with pin and seal lock, as shown in FIG. 6 and FIG. 8. To provide increased stability for the core 47 (FIG. 6), a set of ball bearing inner core compression assemblies 50 (FIG. 6) are seated in sockets 148 in the main frame 41 as shown in FIG. 7. The ball bearings nest in cups 59 in the wall of shell 45 as shown in FIG. 9. Thus the ball bearing inner core compression assemblies 50 (FIG. 6) provide lateral stability to the core 47 (FIG. 6) while allowing air to circulate through the device.

Figure 10:
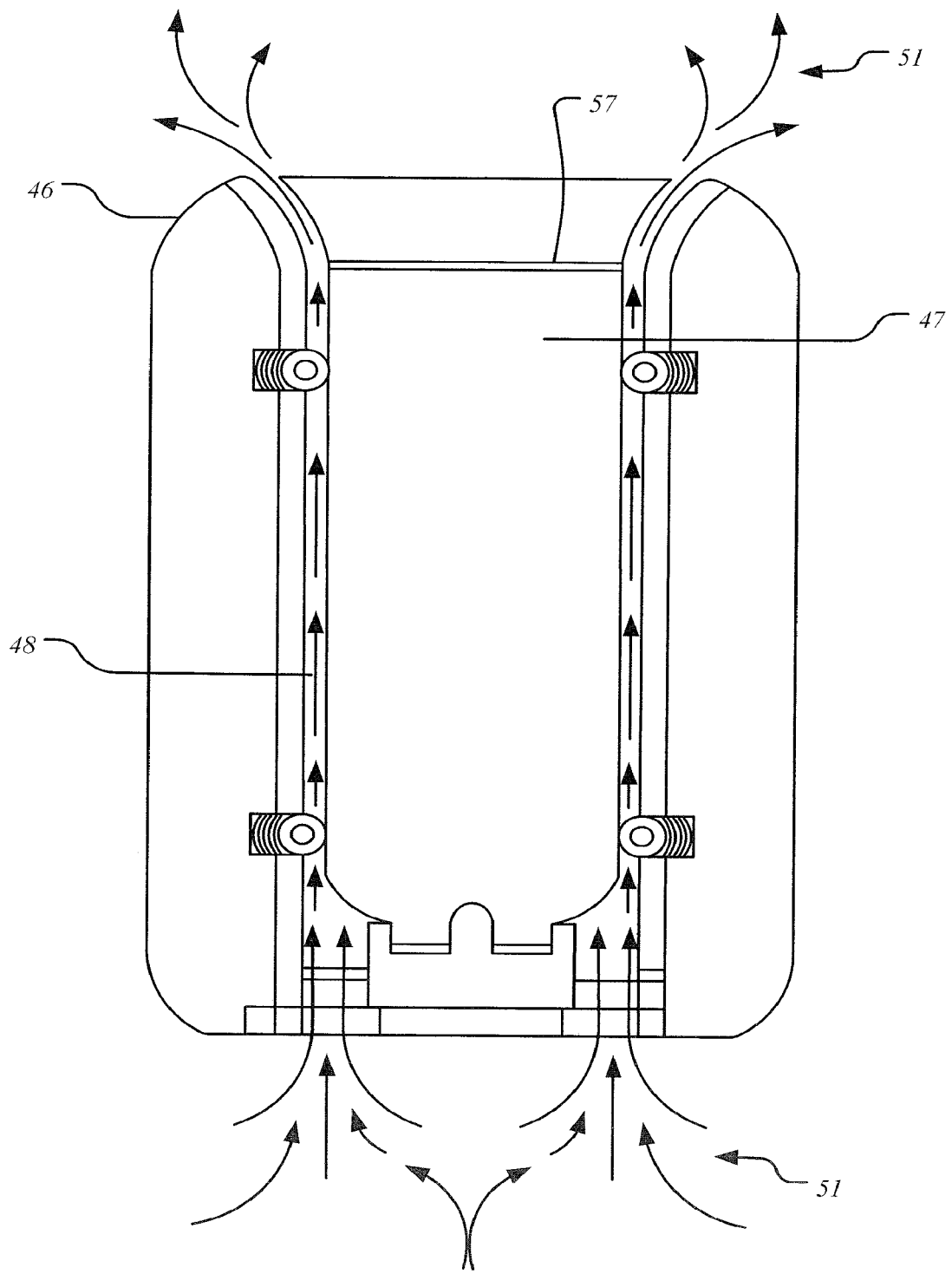
FIG. 10 is a cross section of the device of FIG. 6 showing the circulation of air and substance through the central air duct.
Figure 11:
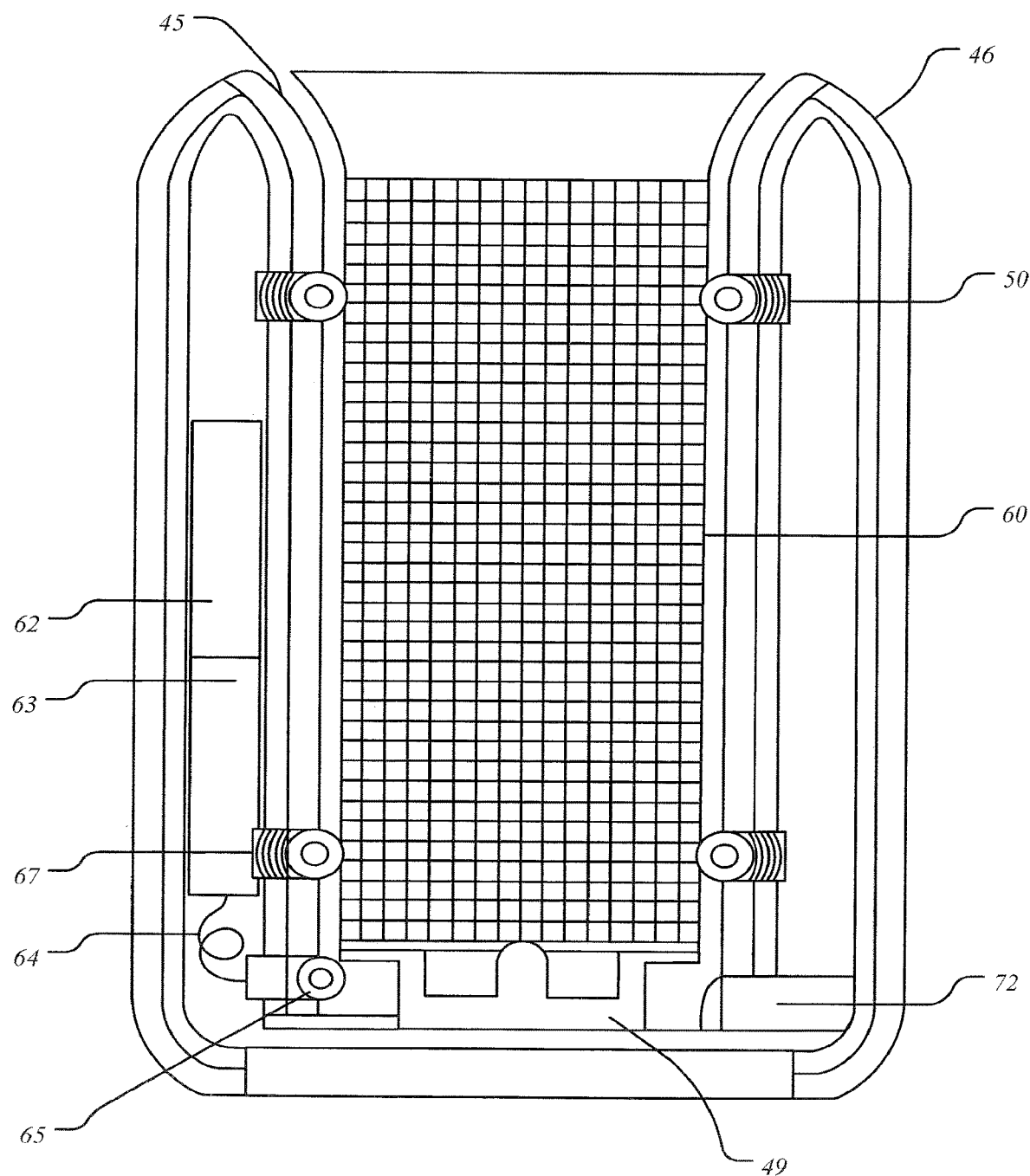
FIG. 11 is a cross section of the device containing an inserted ozone functional module and main supporting hardware.
Figure 12A:
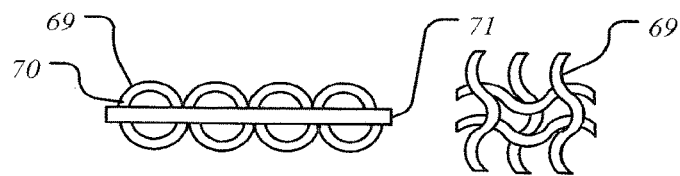
FIG. 12A is an exploded view of the side wall of the module.
Figure 12:
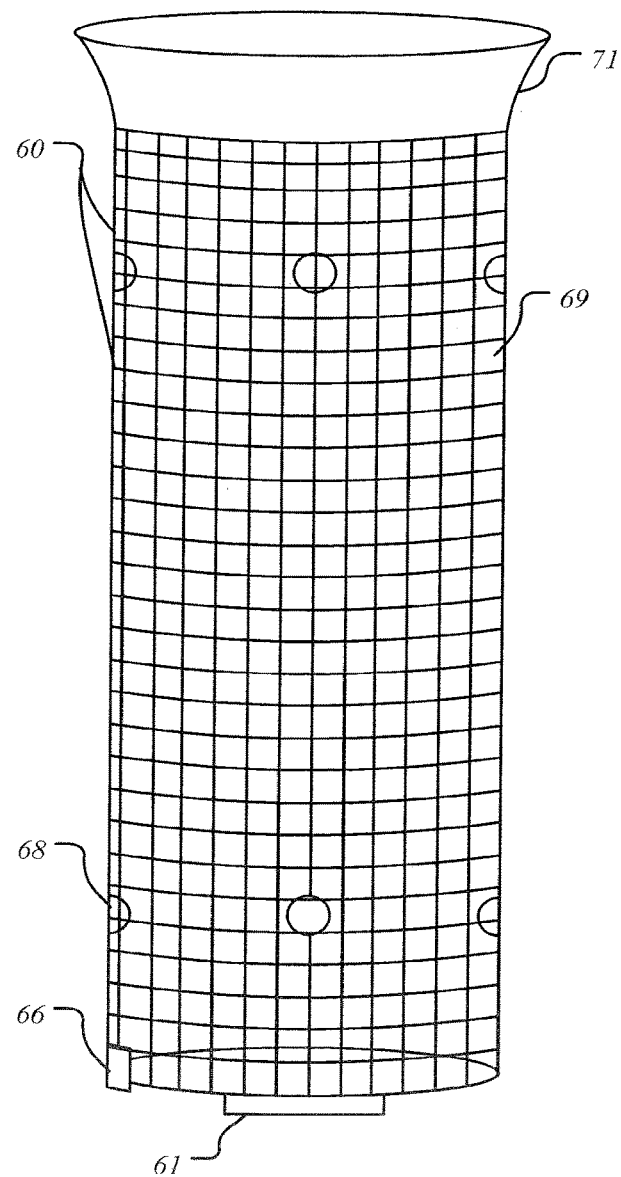
FIG. 12 is a front perspective of the ozone module.

This unimpeded flow of air is seen in FIG. 10 as circulation of air flow 51 around the core 47. The core 47 may, in other embodiments, take a different form where the air flow may be through the core as well, as will be explained hereafter.

Figure 4:
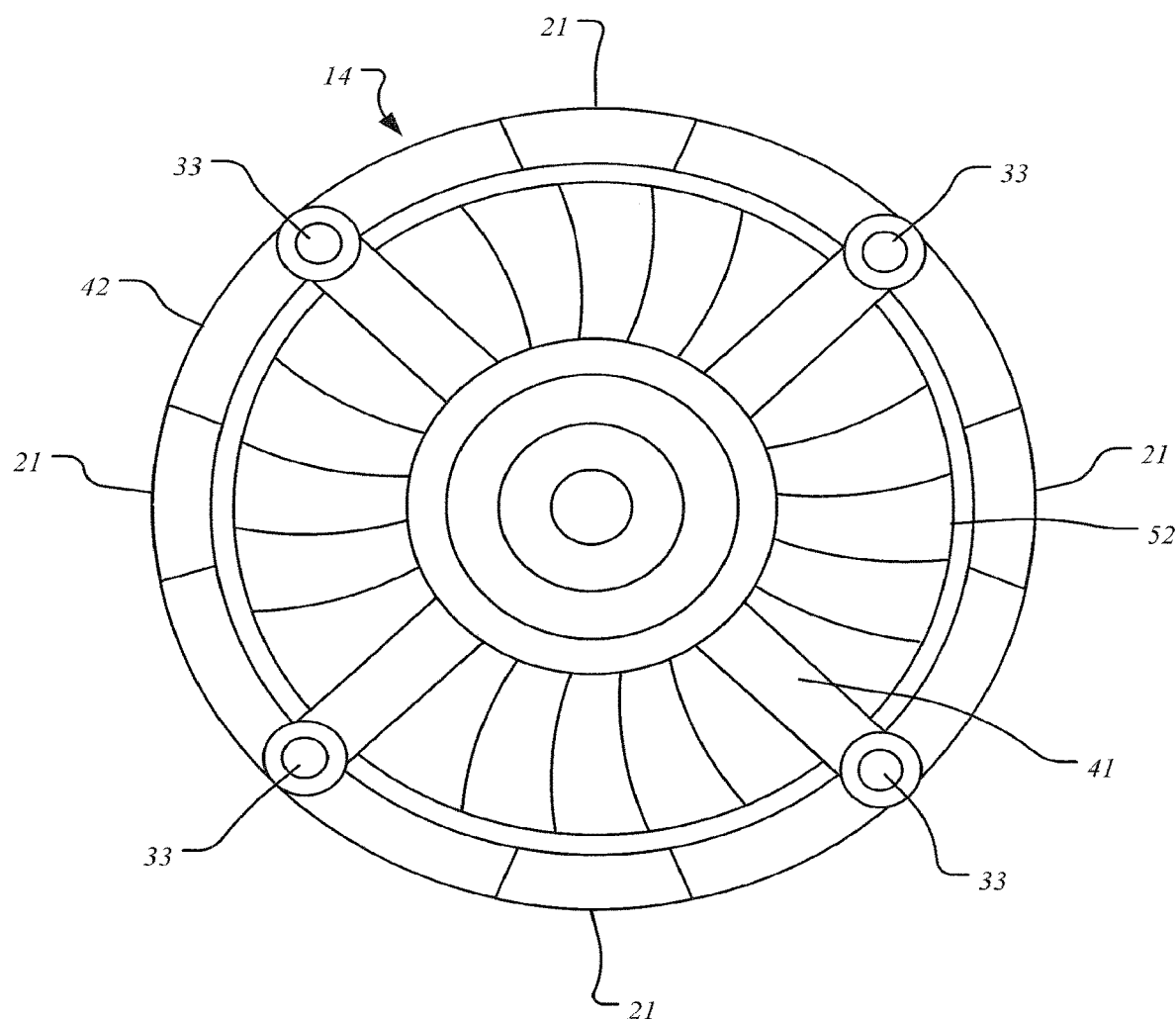
FIG. 4 is a bottom view of the modular device.

A fan 52 with noise reducing blades is integrated in the base of the main frame 41, as shown in the coronal cross section of the main frame 41 in FIG. 7. This fan 52 with noise reducing blades is shown in FIG. 4 in a bottom view and FIG. 7A in a top view. The fan is preferably controlled by pulse modulation, allowing a user to precisely control flow through the central air duct 48, as seen in FIG. 9, through a main core, or around the main core as seen in FIG. 10.

Figure 13:
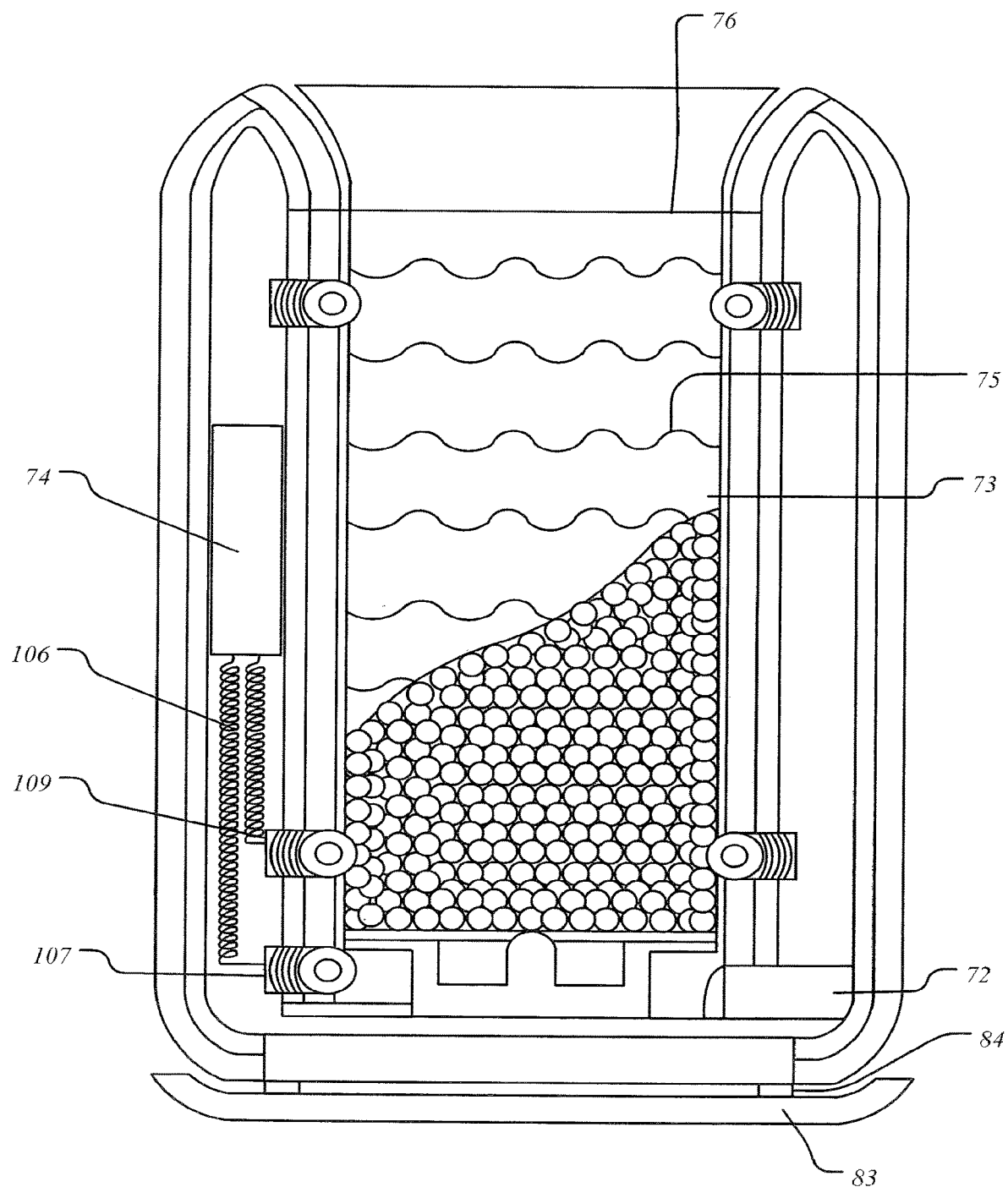
FIG. 13 is a cross section of the device containing a calcium chloride module showing a partially exposed active inner core area and main supporting hardware.
Figure 14:
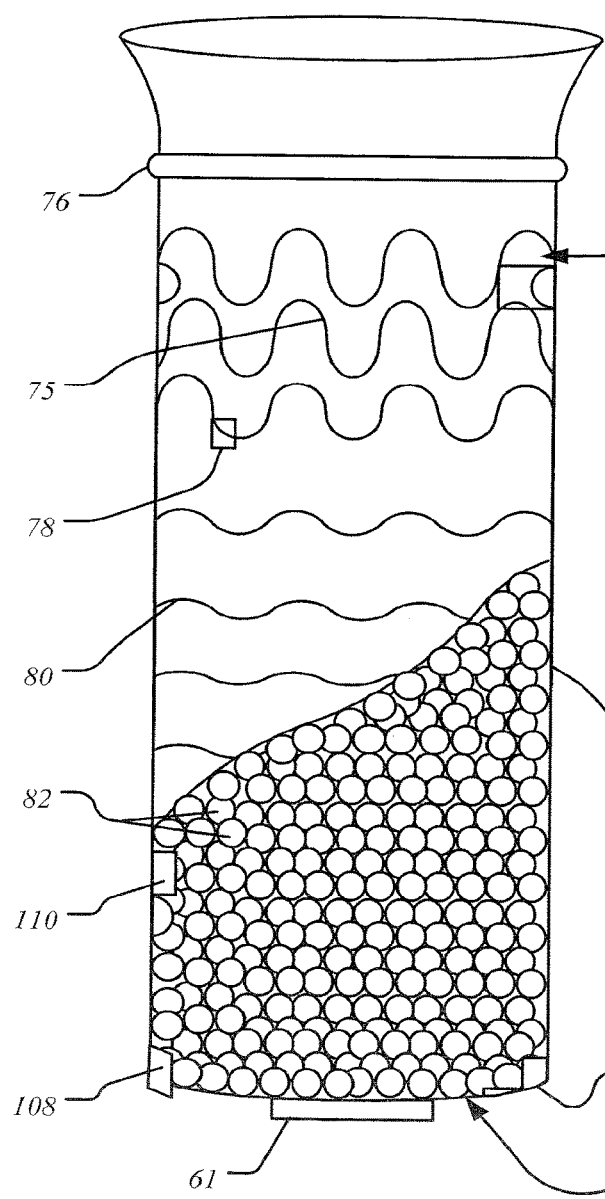
FIG. 14 is a front view of the calcium chloride module showing a partially exposed active inner core area.
Figure 14A:
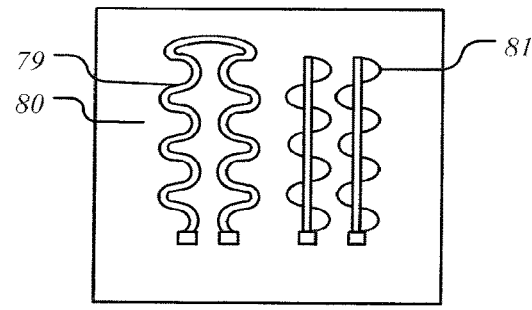
FIGS. 14A, 14B and 14C are exploded views of certain structural parts of the module of FIG. 14.

Controlling the air flow in this preferred embodiment is essential. Air flow controls the rate of pressurized decontamination substances being released from an injection and dispersion assembly as shown in FIG. 8. The injection and dispersion assembly includes threaded core receiver 49 that interfaces with the functional core 47 (FIG. 6), allowing the substance contained in the core under pressure to enter the input duct 54 and reach the injector assembly 55. When energized, the injector assembly 55 allows the flow of pressurized substance to move into the output duct 56 and be dispersed into the air duct 48 (FIG. 9) by a dispersion ring 57 with orifices 53, shown in FIG. 8 and FIG. 8A in cross section and top view. The dispersion ring 57 with orifices 53 is integrated into the inner duct shell 45 (FIG. 9). The rest of the injection and dispersion assembly is housed in the main frame 41 as shown in FIG. 6. The relationship between the main frame 41 and the injection and dispersion assembly is best seen in FIG. 6.

During normal operation, the components of the injection and dispersion assembly—shown in FIG. 8 allow a user to precisely control discharge of the substances from the core structure 47 (FIG. 6). Furthermore, by pulse modulating the injector assembly 55, the user is capable of adjusting the size of the droplets dispersed by the dispersion ring 57 into the air flow 51 as shown in FIG. 10. Utilizing an injector instead of an actuator assembly is an improvement because an actuator assembly's valves can get stuck in an open position. The injector provides a safety feature to the device. The default non-energized state of the injector is always in a closed position. It will not get stuck in an "open" position.

The combination of air and substance flow control, combined with output flow modulating features, such as output bore with directional air flow guiding fins 58 (FIG. 2), makes the device efficient and versatile when it comes to aerosol based decontamination, as compared to a basic spray canister, for example. Due to the tubular structure of the design, made possible by the inner duct shell 45 (FIG. 6), a user is allowed to scale up output capacity by stacking these devices. Device stacking is done in such a way that the product of one device comes out of the output bore directional air flow guiding fins 58 (FIG. 2) at the top of one device and is fed directly into the lower air intake of a fan 52 (FIG. 4) of another unit. These stacked devices are synchronized by light communication over reflective light assembly 21, 22 (FIG. 3) described earlier. This synchronization of devices is not limited to device stacking. The units can still function as a single device when placed, for example, in multiple locations within a target environment.

During decontamination by an agent of choice, additional steps beneficial to the decontamination may be taken, such as adding ozone to combat odor and a dehumidifier combined with an acid reducing agent, for example. In order to add these features, the current invention allows for a user to swap out the functional core 47 (FIG. 6). In case ozone production is desired the core structure 47 FIG. 6) is simply removed and replaced with an ozone core 60, shown in FIG. 11. The ozone core 60 is attached via inner threaded core assembly 61 (FIG. 12) directly to the matching assembly 49 (FIG. 6) inside the core receiver 46 (FIG. 10, FIG. 11). The inserted ozone core 60 and main supporting hardware are shown in FIG. 11. The supporting hardware includes a fast switch controller board 62 that is paired with a high voltage step up board 63, that by a high voltage output wire 64 connects to a high voltage positive conductive ball bearing connector assembly 65. This high voltage positive functional conductive ball bearing connector 65 is in contact with the high voltage contact area 66 on the ozone core (FIG. 12). As a result, the ozone core 60 is connected to the positive side of the high voltage step up board 63 (FIG. 11). Ground connection is provided in a similar fashion by a high voltage ground conductive ball bearing connector assembly 67 (FIG. 11) that is in direct contact with high voltage ground contact 68 on the ozone core 60 (FIG. 12).

This design results in high voltage being supplied to high voltage conductive mesh 69 shown in FIGS. 12 and 12A. The mesh 69 is affixed in place by silicon dielectric adhesive 70 onto a ceramic insulator tube 71, shown in FIG. 12A. The mesh is fastened in the same fashion on the outside and inside of the ceramic insulator tube 71. As a result the inside and outside surfaces of the ceramic insulator tube 71 are covered by electrical conductive mesh 69. The conductive mesh on each side are not connected together. During operation, one side of the tube is positively charged while the other is negatively charged. Utilizing a tube instead of plates helps ergonomics, as well as efficiency. The tube structure provides increased surface area per volume. Once the ozone core 60 is energized, all ozone produced is pushed by the fan 52 with noise reducing blades, shown in FIG. 7, through the output bore with directional air flow guiding fins 58 (FIG. 2) while new ozone deficient air is introduced through the lower air intake base of fan 52 (FIG. 4). The air circulation through the device with an ozone core 60 (FIG. 12) functions in the same way as when a core 47 (FIG. 6, FIG. 10) is inserted to dispense decontaminant agents, as can again be seen in FIG. 10 with the air flow 51. For data purposes, ozone readings are collected by an ozone sensor located in the sensor assembly 72 (FIG. 11, FIG. 15) at the base of the inner shell 45 (FIG. 11) just above the fan 52 with noise reducing blades.

A dehumidifier combined with acid reducing agent can be provided in a similar fashion. The only step required is to replace the functional core 47. For a dehumidifying function, a calcium chloride ($CaCl_2$) dryer core 73 may be used as shown in FIG. 13, in a coronal cross section of the device. The $CaCl_2$ dryer core 73 uses most of the same components as the ozone core 60 (FIG. 12). The $CaCl_2$ dryer core 73 utilizes a high amperage switch control board 74 that is responsible for the power supply to the functional core heating element 75 (FIG. 14). A high amperage output wire 106 (FIG. 13), high amperage positive conductive ball bearing connector 107 (FIG. 13), high amperage ball bearing positive contact area 108 (FIG. 14), high amperage ground conductive ball bearing connector 109 (FIG. 13), and a high amperage ball bearing ground contact area 110 (FIG. 14), respectively complete the circuit to the dryer core 73. The dryer core 73 is filled with $H_2O$ absorbent $CaCl_2$ particles 82 shown in detail on FIG. 14. Airflow is forced to flow through the inner part of the core by utilizing an inner shell duct neck seal 76 (FIG. 13, FIG. 14) placed around the upper part of the $CaCl_2$ dryer core 73. This forces the moist acidic air to enter via the fenestrated $CaCl_2$ dryer core base 77 (FIG. 14B). This way the $H_2O$ absorbent $CaCl_2$ particles 82 absorb the water, and react with substances such as acetic acid, for example, to produce $CO_2$.

Figure 14C:
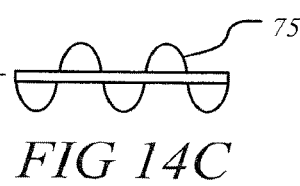
Figure 14B:
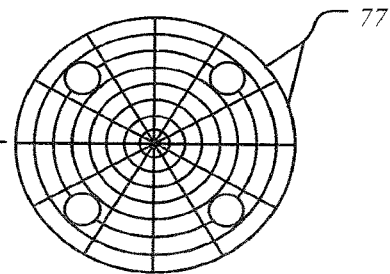

Optimization of this process is achieved by having the $H_2O$ saturated $CaCl_2$ dryer core 73 heated up by energizing the functional heating element 75 (FIGS. 14 and 14C). This heating speeds up the reaction between the acetic acid in the air and $CaCl_2$ particles 82 and dries the $CaCl_2$ particles 82, thus allowing the core to be reused. To prevent overheating and fire, a thermal fuse 78 (FIG. 14) is located on the upper part of the $CaCl_2$ dryer core 73. This thermal fuse 78 will be activated in case of overheating and will break the continuous circuit of the heating element 75. Optionally, to decrease the cost of production, the heating element is made of electro-conductive resin 79 (FIG. 14A) that is printed on a thermal conductive dielectric insulator surface 80 (FIG. 14A).

For data collection purposes, a pH sensitive strip sensor 81 (FIG. 14A) is utilized. This strip functions in a similar way to batteries. Two strips are printed in parallel to each other on the thermal conductive dielectric insulator surface 80, on the inside part of the core. Once acid is deposited between them, it acts as an electrolyte causing a small electric potential correlated to pH that is sensed. Another optional sensor is a moisture sensor 105 located on the lower side of the $CaCl_2$ dryer core 73. This sensor is printed in similar fashion to the pH strip sensors 81. However instead of potential, the electrical resistance between the two parallel strips is sensed. Thus, as moisture deposits increase, resistance will decrease, correlating with the moisture in the air. The temperature of the air entering the $CaCl_2$ dryer core 73 is sampled by inner duct temperature sensor 72 (FIG. 13). Another distinctive feature of the $CaCl_2$ dryer core 73 is the auxiliary liquid collection plate 83 (FIG. 13) that is attached to the base of the dryer core by permanent magnets 84 (FIG. 13). The metal plate assembly collects any water that may come down from the $CaCl_2$ dryer core 73 (FIG. 13) via the fenestrated $CaCl_2$ dryer core base 77 (FIG. 14B) without impeding air flow.

Figure 15:
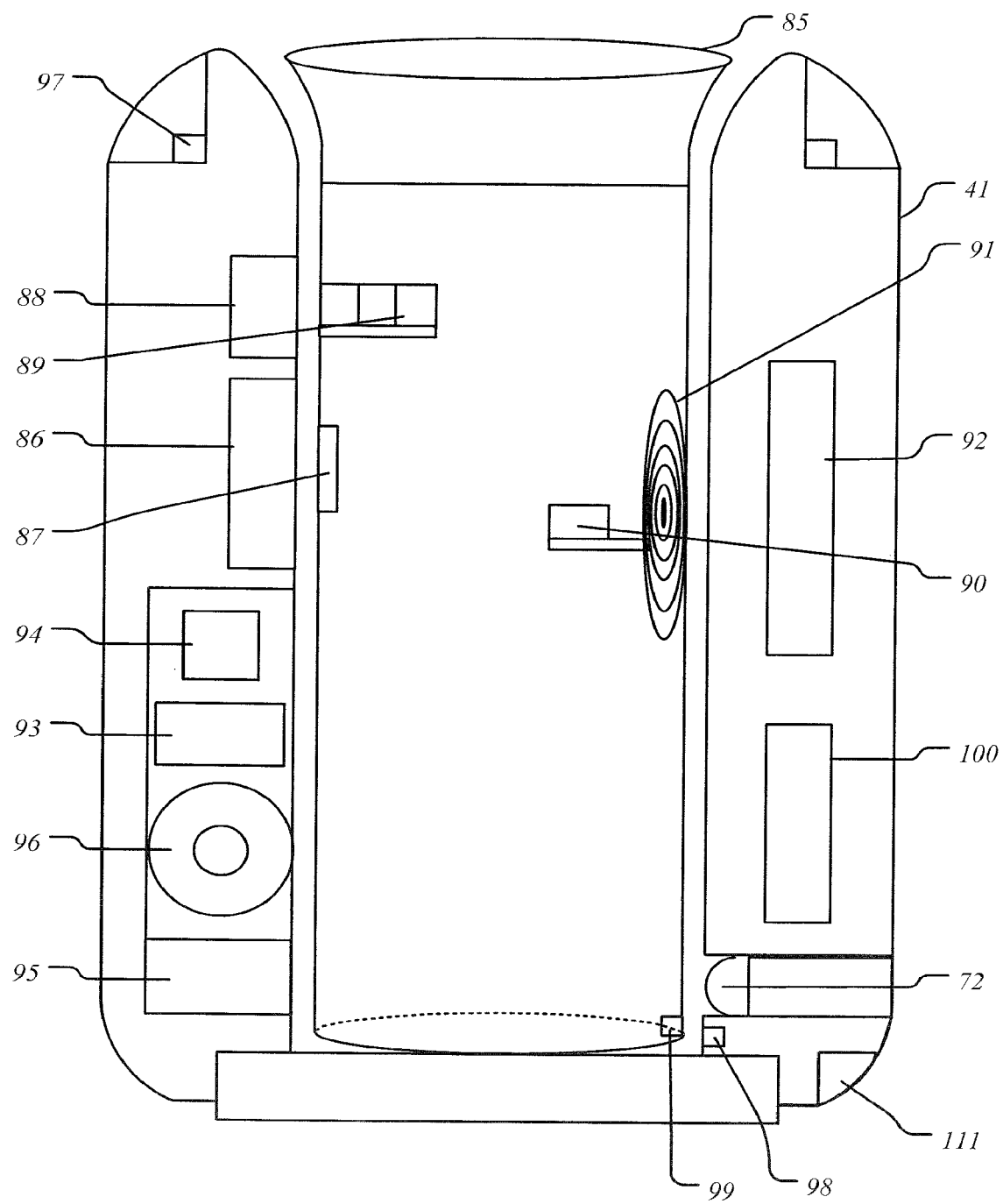
FIG. 15 is a cross sectional view of the device showing the main electrical components in the module receiver and main frame of the module receiver.

FIG. 15 illustrates the major electronic components and their spacial relationship in the main frame 41, and the core assembly 85. These components include an RFID reader 86. This allows the device to recognize the type of core inserted and provides verification to prevent counterfeited third party hardware utilization, simply by reading the RFID tag 87 on the core 85. The RFID reader 86 is also capable of reading RFID tags located on a user's badge, thus identifying the user and user privileges for operation. This prevents unauthorized personnel from operating the device. A light emitter and receiver 88 uses an infrared light spectrum to read ID strips 89 located on the core 85. The process is similar to bar code reading, where the emitter emits light and the receiver reads the light reflected from the pattern on the ID strips 89. The ID strips 89 can be replaced by testing strips that, for example, change color due to reaction to a pathogen or chemical. Another way to identify a general core assembly structure 85 is by an accessory micro controller 90 that is paired with a charging coil 91 and an induction coil 92, all located inside the main frame 41 parallel to each other. In this case an EMP field is generated by the induction coil 92 creating a potential in the charging coil 91. This powers the accessory micro controller 90 that performs the identity function described above. The induction coil 92 can turn generated magnetic pulses into potential that is read by an auxiliary micro controller 93. This auxiliary micro controller 93 has input/outputs utilized to interface with various peripheral components. This auxiliary micro controller 93 is indirectly interfaced by an OTG micro controller 94 that, by its USB peripheral 95, utilizes USB hardware such as, BT™ or Wi-Fi, for example. This additional hardware allows it to communicate with smart devices as well as allowing for remote storage and retrieval of data.

A piezo speaker assembly 96 has double functionality. It is used to provide audio feedback to a user and detect sound. Detecting sound is one of the multiple variables that is utilized to reassure proper response to the environment and provide a built-in safety feature. In addition to sound as a safety feature, the device can respond to movement and light by the reflective light assembly 21, 22 (FIG. 3) housed in the main frame 41 (FIG. 15) in light assembly sockets 97 (FIG. 15). A magnetic responsive switch 98 (FIG. 15) is adjacent to a magnet 99 (FIG. 15) or the core 85. The magnet 99 (FIG. 15) is placed in spacial relationship to the magnetic responses switch 98, enabling the switch to respond to a magnetic field and detect the presence of the core 85. Detection of hardware inside the central air duct 48 (FIGS. 6 and 9) can be achieved by utilizing the light emitter and receiver assembly 88 (FIG. 15), detecting the reflection of the surface of the core 85. This function may also be a safety feature of the device. Various accessory peripheral sensors provide data that can be integrated into the functional cycle of the device as well as displayed on a user's smart device screen, or other type of screen, such as the visual feedback device 44 (FIG. 1).

The current embodiment preferably utilizes an DHT 22 sensor 100 (FIG. 15). This digital sensor provides data, such as humidity, temperature, body heat index, for example. An additional auxiliary moisture sensor 111 (FIG. 15) is located at the bottom of the main frame 41 for detecting moisture levels on the auxiliary liquid collection plate 83 (FIG. 13).

Figure 16:
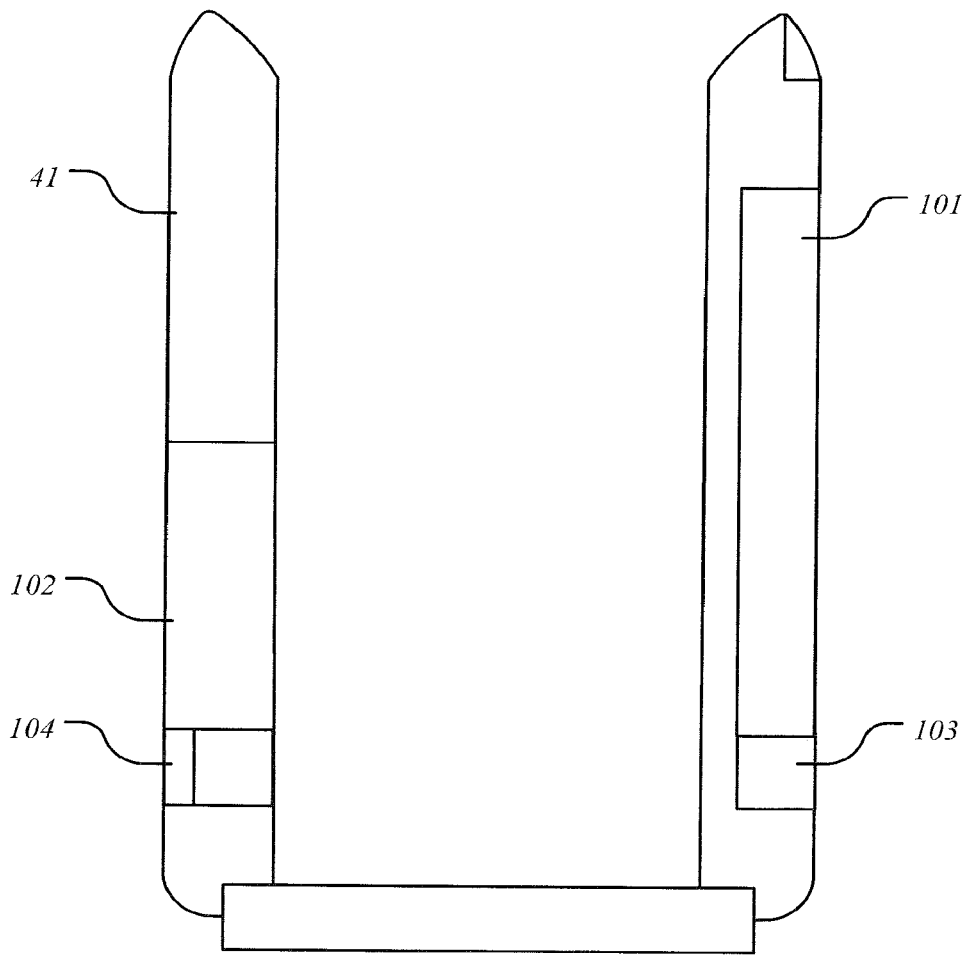
FIG. 16 is a cross sectional view of the device showing the power and charging components within the module receiver.

To meet the power demands of the device, a combination of batteries and an external power supply are provided. FIG. 16 shows the distribution of power and charging components within the main frame 41 in cross section. A battery source 101 is connected to a step-up and power modulation, control, and charging PCB 102 that makes sure a stable, uninterrupted power supply is available to all of the electrical components. A fuel gauge and battery management CPU 103 is utilized to collect data from the battery source such as cycles, charging state, and other battery management data for example. This data can be displayed graphically and/or numerically to the user. A main power supply plug/coupling 104 is utilized for the purpose of connecting the power supply to a power source during higher power demands or charging the battery, for example. In addition it allows, by adapter cables (not shown), to interconnect to additional devices, therefore enabling multiple devices to share a single main direct power supply. The cylindrical design of the device as previously described, has enough surface area to accommodate all of the components described herein, therefore allowing them to be easily integrated into the main frame 41.

Figure 17:
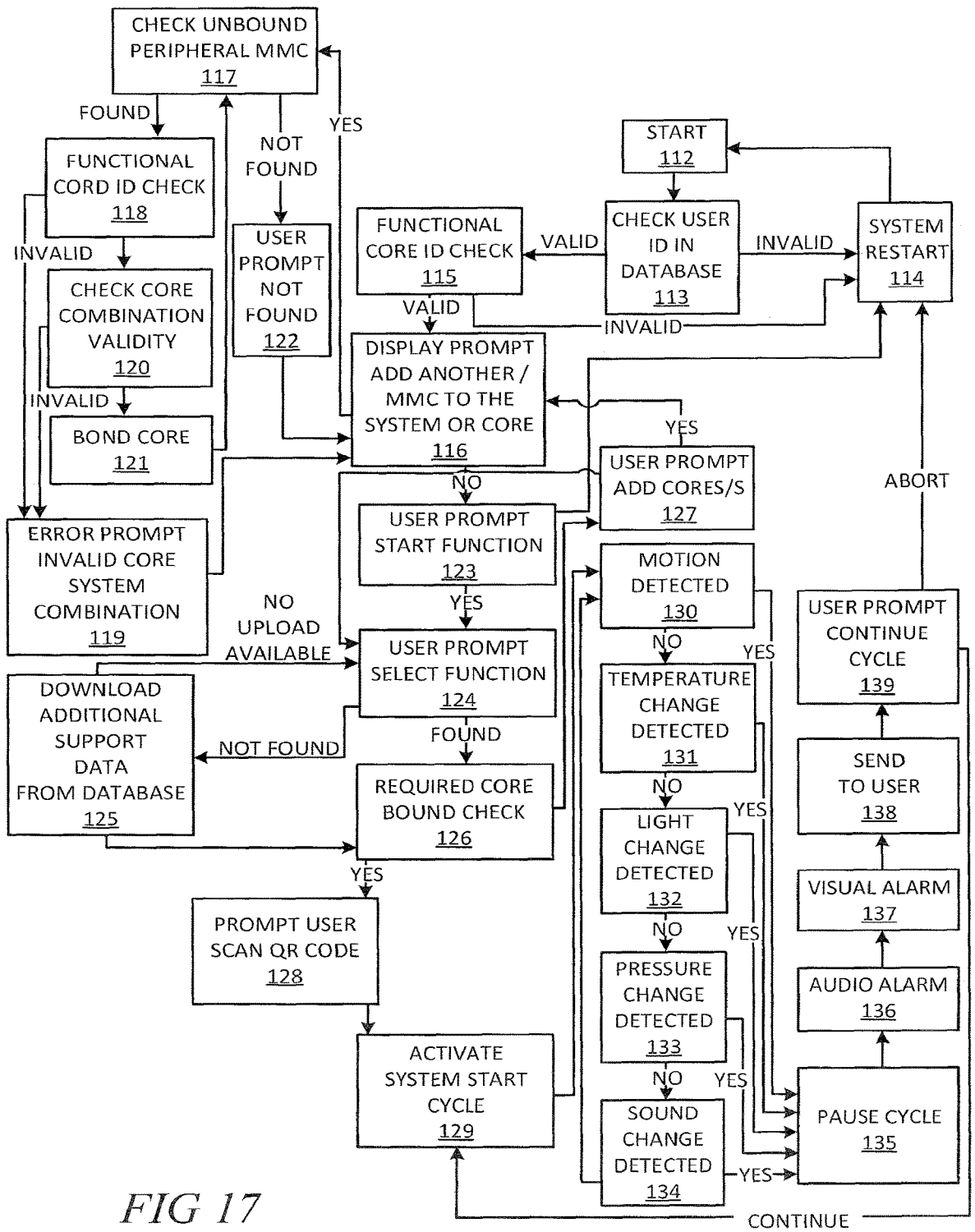
FIG. 17 is a flow chart of the major software logic used by the device during operation.

Operation of this device in all its respects is represented by a diagrammatic overview shown in FIG. 17. FIG. 17 is a representation of the major software logic steps during normal operation, including trigger and fail safe functions. The first step 112 is activation of the device followed by self-check and calibration, depicted by "start." The next step 113 after initialization is to obtain by RFID the identification number of the user, thus defining privileges, by way of a local or remote database through a smart device. If ID is not confirmed then no user privileges are granted, and after reporting the incident, the system is forced to restart 114 which sends the device to the initialization step 112. On the other hand, if the ID is confirmed, specific user privileges are granted. Therefore each user can operate the device based on their training and responsibility. Once privileges are given, the device enters the next stage, functional core ID check 115. This step reassures that the functional core inserted is authentic, as well as capable of functioning to complete the tasks it was designed for. Furthermore, if a multi-step process or increased scalability by utilizing additional cores is available, then the device prompts the user to add more devices to the system 116. During this step the device is utilizing multiple types of communication as well as data stored regarding its previous configuration to communicate with other units and check their state shown by check unbound peripheral MMC 117. If no additional ready devices are found, then a message prompt, no additional MMC's found 122 is displayed. The user is then directed to step 116 that prompts the user to add more devices. If in step 117, additional devices with functional cores that can be used in the task are found, their functional core IDs are read 118 and verified. During this step if there is a failure due to incompatible core or other parameters rendering the core unusable, an error prompt 119 is displayed. In this case the prompt states "Error in additional core or system combination," and user is looped to step 116. However, if the functional and ID check step 118 has been verified with the database, then a basic failsafe check is performed 120 that reassures that this combination of components is allowed. It is important to note that this step does not rely on additional data from a database but rather utilizes the data from the device. Even if the database is corrupted or no access is available, the device can prevent misuse. If step 120 fails then it forces the user to go to step 119 and loops to step 116. However, if during step 120 the combination of additional devices with functional cores is permitted then the devices are bonded 121. Thus the units establish communication with each other and become, essentially a single unit.

At this point the user is forwarded to step 117, allowing for additional devices with functional cores to be added. The data of the bonded devices is stored locally as well as sent to, and retrievable from, a remote database utilizing a smart device. It is important to mention that the configuration, its various devices, its components and their state has a visual depiction that is not shown. If during step 116, which prompts the user to add additional devices, is responded negatively with "No," then the user is forwarded to step 123 which produces a prompt that explains the function as well as requests confirmation by the user to start the procedure which is, in this case, releasing decontamination substances. If response to the start function 123 is negative, "No," the user is sent to step 114 system restart. However if the user confirms the procedure then the user is given a variety of functions that can be performed with the current hardware configuration 124. If there is enough data stored in the devices to perform the multistep task, then the devices communicate with each other and after verifying the integrity of the libraries utilized by the micro controller the user moves from step 126 to step 128. However, if during step 124 the function chosen by the user cannot be performed due to the lack of additional data regarding the operation of the individual micro controllers of the bonded devices, a request to obtain data from local or remote data storage is sent at step 125. If data cannot be obtained, the user is sent back to the function prompt 124 to choose another function (note: the function previously selected is disabled and grayed out). If data upload is successful then data is uploaded to the micro-controller and the user is moved to step 126 which verifies that the newly uploaded functional commands are matched to the bonded functional cores. If mismatch is detected, the user is sent to step 127 which prompts the user for a proper core to be added or replaced, looping the cycle to step 116 and prompting the user to add a functional core or MMC with the necessary core. On the other hand, if step 126 is completed without errors then the user moves further into step 128 which is part of the trigger mechanism.

In this embodiment, software and hardware of smart devices are utilized. The software and camera combination QR code IDs are used. In this case, a smart device is used as a remote start button reassuring that the user has left the decontamination area, by simply reading a QR ID sticker placed outside the decontamination area, which may be a surgical room for example. Thus in order to read the code the user physically has to pass by the door and be outside of the room in order to scan the code. Once the code is scanned, a warning is displayed prompting the user to confirm activation of the trigger. This causes the smart device by various modes of communication, such as light, sound and radio frequency, to send a specific unique command remotely to the bonded device it is paired with and thus activate it. As a result, from the step 128, the trigger system is activated 129. In the preferred embodiment this leads to dispersion of decontaminating agent from a pressurized container (not shown). During the decontamination cycle a timed monitor system reads various parameters during decontamination, using motion sensor 130, a temperature sensor 131, an optic thermopile to sense light changes 132, barometric pressure changes 133, and sound changes 134. Utilizing this data, the device is capable of detecting if surgical or lab doors are opened, or if somebody has entered the area. The combination of the capabilities mentioned above allow for more precise, accurate responses to the gathered data. This data is preferably sent by a smart device, to a local and/or remote storage, such as to the cloud or database in a standard format. Such a database can be utilized by parties authorized access, such as the EPA. This device allows for monitoring of the processes and by the geolocation capabilities of the device and a smart device enabling unsurpassed accountability. If any of the monitored data goes out of a predetermined value range, an array of audio and visual warnings are displayed on the device as well as the smart device, or the remote monitoring system (not shown). This may include audio alarm 136 and visual alarm 137 for example. The authorized users receive a warning as well as a message 139, forcing the user to reactivate the cycle which was paused 135 or to abort it thus taking the user back to system restart 114.

Other sensors such as described previously can be combined and utilized to improve the monitoring capabilities. Access to a third party supplier, such as producers of other substances or hardware can be granted, therefore allowing the device to provide support for other decontamination applications and substances. Furthermore the ability of the smart device to communicate with the MMC allows third parties to write various applications that utilize data from selected sensors. For example, the temperature sensor can double as a fire alarm, motion sensor can function as a burglar alarm, and the smart device utilizing the light sensor can operate the lights in the room that are paired with the smart device.

Figure 18:
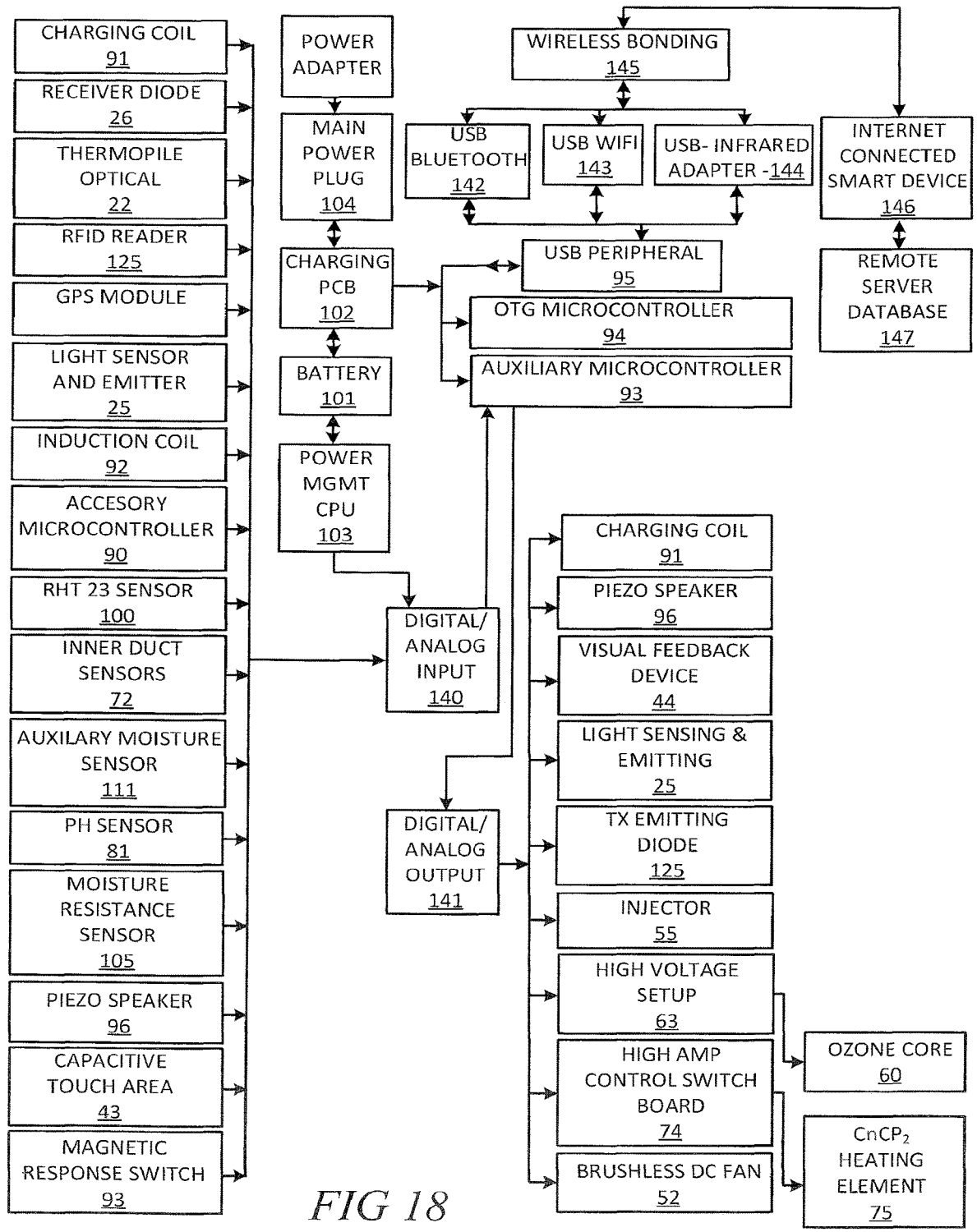
FIG. 18 is a block diagram of the device components.

A block diagram of the system hardware components are shown in FIG. 18, emphasizing the dual use of selected components, such as piezo speaker 96 that functions to produce audible noise during alerts, can be used for communication by ultrasound, and as a microphone to detect sound. Another example of multiple use of a component is the induction coil 92 and charging coil 91 that when combined with accessory micro-controller 90 can be used for two way communication utilizing electromagnetic pulses, besides charging.

The block diagram of FIG. 18 describes the main structure that provides the major functions of the device. Digital/Analog input channels 140 collect data from the various peripheral components, and sensors. This data is fed into the auxiliary micro-controller 93 that further processes the data, utilizing its firmware. The micro-controller 93 responds by sending data to output channels 141 that are interconnected with various peripheral components. The auxiliary micro-controller 93 is interconnected with OTG micro-controller 94 allowing data exchange based on the users preferences. The OTG micro-controller 94 is capable, due to its OTG libraries, to support USB hardware, such as, but not limited to, USB Bluetooth 142, USB Wi-Fi 143 and USB Infrared adapter 144. This hardware is connected by a USB peripheral 95 that is a standard plug. This standard hardware is capable of establishing wireless bonding 145 with an Internet connected smart device 146 that can remotely store or retrieve data in a standard format, upon request. Custom firmware may be utilized at the auxiliary micro-controller 93, which is responsible for the majority of the functions of the device. The OTG controller's main function is to support various standard hardware that is utilized to allow communication with an Internet connected smart device 146. This Internet connected smart device 146 acts as a modem to further allow remote storage and retrieval of data. The Internet capable smart device provides a user friendly interface.

What is claimed is:

1. A modular device, comprising:
   a frame having walls, an open center, a top, and an open base;
   a fan at the open base of the frame;
   a connector in the center of the frame, above the fan for connecting to different functional cores;
   a duct connected to the connector;
   a dispersion ring having a plurality of orifices located at the top of the frame connected to the duct for releasing dispersant into the open center of the frame along the walls of the frame;
   an outer shell for covering the frame having an open top and open base coincident with the top and open base in the frame; and
   support bearings mounted to the open base of the frame for movably supporting the frame,
   whereby the fan forces air through the open base of the outer shell into the open center of the frame, and out the open top of the outer shell.

2. The modular device of claim 1 further comprising:
   a canister containing a dispersant located in the open center of the frame attached to the connector for releasing dispersant into the duct and the dispersion ring;
   whereby the dispersant is released by the dispersion ring into the airflow in the open center of the frame.

3. The modular device of claim 2 further comprising an injection pump located in the duct between the connector and the dispersion ring, whereby the injection pump modulates the droplets of dispersant released by the dispersion ring.

4. The modular device of claim 2 further comprising a plurality of airflow guide fins located at the open top of the frame, whereby the guide fins direct the airflow out of the open top of the frame.

5. The modular device of claim 2 wherein the fan at the open base comprises a brushless DC motor.

6. The modular device of claim 2 further comprising:
   compression assemblies mounted on the walls of the frame for compressive engagement with the canister in the open center of the frame.

7. The modular device of claim 6 wherein the canister contains indentations that coincide with the location of the compression assemblies on the walls of the frame, whereby the compression assemblies engage with the indentations of the canister thereby stabilizing the canister.

8. The modular device of claim 1 wherein the support bearings comprise:
   a bearing housing;
   a ceramic ball contained in the bearing housing;
   a frictionless plate surrounding the ceramic ball in the housing;
   a compression member in the housing exerting a force on the ceramic ball; and
   attachment means for attaching the bearing housing to the base of the frame.

9. The modular device of claim 1 further comprising:
   light assemblies at the top and at the base of the frame, each light assembly containing light scattering particles located between light reflecting walls and a light conductive wall.

10. The modular device of claim 9 wherein the light assemblies include a light sensor and light emitter, a light receiving diode, a light transmitting diode, and a motion sensor.

* * * * *